(12) United States Patent
Chen et al.

(10) Patent No.: US 11,027,125 B2
(45) Date of Patent: Jun. 8, 2021

(54) INTERVENTIONAL MEDICAL DEVICES, DEVICE SYSTEMS, AND FIXATION COMPONENTS THEREOF

(71) Applicant: Medtronic, Inc., Minneapolis, MN (US)

(72) Inventors: Xin Chen, Blaine, MN (US); Michael D. Eggen, Chisago City, MN (US); Vladimir Grubac, Brooklyn Park, MN (US); Brian P. Colin, Shakopee, MN (US); Wei Gan, Woodbury, MN (US); Thomas A. Anderson, New Hope, MN (US); Kathryn Hilpisch, Cottage Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 164 days.

(21) Appl. No.: 16/158,724

(22) Filed: Oct. 12, 2018

(65) Prior Publication Data
US 2019/0046789 A1 Feb. 14, 2019

Related U.S. Application Data

(63) Continuation of application No. 15/410,161, filed on Jan. 19, 2017, now Pat. No. 10,099,050.
(Continued)

(51) Int. Cl.
*A61N 1/05* (2006.01)
*A61N 1/362* (2006.01)
(Continued)

(52) U.S. Cl.
CPC .......... *A61N 1/0573* (2013.01); *A61N 1/362* (2013.01); *A61N 1/3756* (2013.01); *A61N 1/37205* (2013.01); *A61N 2001/058* (2013.01)

(58) Field of Classification Search
CPC .... A61N 1/057; A61N 1/0573; A61N 1/3756; A61N 1/362
(Continued)

(56) References Cited

U.S. PATENT DOCUMENTS

| 3,717,151 A | 2/1973 | Collett |
| 3,754,555 A | 8/1973 | Schmitt |

(Continued)

FOREIGN PATENT DOCUMENTS

| CA | 1003904 A1 | 1/1977 |
| CN | 1882370 | 12/2006 |

(Continued)

OTHER PUBLICATIONS

Prosecution History from U.S. Appl. No. 15/410,085, dated from Nov. 2, 2018 through Feb. 7, 2019, 17 pp.
(Continued)

*Primary Examiner* — Amanda K Hulbert
*Assistant Examiner* — Philip C Edwards
(74) *Attorney, Agent, or Firm* — Shumaker & Sieffert, P.A.

(57) ABSTRACT

A fixation mechanism of an implantable medical device is formed by a plurality of tines fixedly mounted around a perimeter of a distal end of the device. Each tine may be said to include a first segment fixedly attached to the device, a second segment extending from the first segment, and a third segment, to which the second segment extends. When the device is loaded in a lumen of a delivery tool and a rounded free distal end of each tine engages a sidewall that defines the lumen, to hold the tines in a spring-loaded condition, the first segment of each tine, which has a spring-biased preformed curvature, becomes relatively straightened, and the third segment of each tine, which is terminated by the free distal end, extends away from the axis of the device at an
(Continued)

acute angle in a range from about 45 degrees to about 75 degrees.

12 Claims, 12 Drawing Sheets

Related U.S. Application Data

(60) Provisional application No. 62/281,403, filed on Jan. 21, 2016.

(51) Int. Cl.
    *A61N 1/375* (2006.01)
    *A61N 1/372* (2006.01)

(58) Field of Classification Search
    USPC .......................................................... 607/126
    See application file for complete search history.

(56) References Cited

U.S. PATENT DOCUMENTS

| | | |
|---|---|---|
| 3,814,104 A | 6/1974 | Irnich |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bomzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,738,672 B2 | 5/2004 | Schulman |
| 6,743,240 B2 | 6/2004 | Smith et al. |
| 6,755,812 B2 | 6/2004 | Peterson et al. |
| 6,823,217 B2 | 11/2004 | Rutten |
| 6,909,920 B2 | 6/2005 | Lokhoff et al. |
| 6,944,507 B2 | 9/2005 | Froberg |
| 6,953,454 B2 | 10/2005 | Peterson et al. |
| 7,027,876 B2 | 4/2006 | Casavant et al. |
| 7,082,335 B2 | 7/2006 | Klein et al. |
| 7,082,336 B2 | 7/2006 | Ransbury |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,130,700 B2 | 10/2006 | Gardeski |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,331,922 B2 | 2/2008 | Mohl |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |

(56) References Cited

U.S. PATENT DOCUMENTS

| | | |
|---|---|---|
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,949,395 B2 | 5/2011 | Kuzma |
| 7,993,351 B2 | 8/2011 | Worley et al. |
| 8,010,209 B2 | 8/2011 | Jacobson |
| 8,012,127 B2 | 9/2011 | Lieberman |
| 8,032,219 B2 | 10/2011 | Neumann |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,170,690 B2 | 5/2012 | Morgan et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,262,672 B2 | 9/2012 | Neidert |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,418,362 B2 | 4/2013 | Zerfas et al. |
| 8,428,750 B2 | 4/2013 | Kolberg |
| 8,452,420 B2 | 5/2013 | Flach et al. |
| 8,478,431 B2 | 7/2013 | Griswold |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan |
| 8,634,912 B2 | 1/2014 | Bornzin |
| 8,670,842 B1 | 3/2014 | Bornzin |
| 8,700,181 B2 | 4/2014 | Bornzin et al. |
| 8,721,587 B2 | 5/2014 | Berthiaume et al. |
| 8,727,996 B2 | 5/2014 | Allan et al. |
| 8,738,147 B2 | 5/2014 | Hastings et al. |
| 8,755,909 B2 | 6/2014 | Sommer |
| 8,758,365 B2 | 6/2014 | Bonner et al. |
| 9,119,959 B2 | 9/2015 | Rys |
| 9,155,882 B2 | 10/2015 | Grubac |
| 9,283,381 B2 | 3/2016 | Grubac et al. |
| 9,414,857 B2 | 8/2016 | Wood |
| 9,446,248 B2 | 9/2016 | Sheldon |
| 9,526,522 B2 | 12/2016 | Wood et al. |
| 9,526,891 B2 | 12/2016 | Eggen |
| 9,539,423 B2 | 1/2017 | Bonner |
| 10,071,243 B2 | 9/2018 | Kuhn et al. |
| 10,099,050 B2 | 10/2018 | Chen et al. |
| 10,463,853 B2 | 11/2019 | Drake et al. |
| 10,518,084 B2 | 12/2019 | Kuhn et al. |
| 2002/0077556 A1 | 6/2002 | Schwartz |
| 2002/0095203 A1 | 7/2002 | Thompson |
| 2003/0004537 A1 | 1/2003 | Boyle et al. |
| 2003/0233139 A1 | 12/2003 | Chitre et al. |
| 2004/0034401 A1 | 2/2004 | Dahlberg et al. |
| 2004/0147973 A1 | 7/2004 | Hauser |
| 2004/0176797 A1 | 9/2004 | Opolski |
| 2004/0230280 A1 | 11/2004 | Cates |
| 2004/0249417 A1 | 12/2004 | Ransbury et al. |
| 2005/0090890 A1 | 4/2005 | Wu et al. |
| 2005/0267555 A1 | 12/2005 | Marnfeldt et al. |
| 2006/0085039 A1 | 4/2006 | Hastings et al. |
| 2006/0247753 A1 | 11/2006 | Wenger |
| 2007/0043414 A1 | 2/2007 | Fifer et al. |
| 2007/0043441 A1 | 2/2007 | Pisharodi |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051863 A1 | 2/2008 | Schneider |
| 2009/0082827 A1 | 3/2009 | Kveen et al. |
| 2009/0082828 A1 | 3/2009 | Ostroff |
| 2009/0204170 A1 | 8/2009 | Hastings et al. |
| 2009/0281605 A1 | 11/2009 | Marnfeldt et al. |
| 2010/0131036 A1 | 5/2010 | Geistert et al. |
| 2010/0198288 A1 | 8/2010 | Ostroff |
| 2010/0211149 A1 | 8/2010 | Morgan et al. |
| 2011/0034939 A1 | 2/2011 | Kveen et al. |
| 2011/0054555 A1 | 3/2011 | Williams et al. |
| 2011/0112548 A1 | 5/2011 | Fifer et al. |
| 2011/0125163 A1 | 5/2011 | Ruffen et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0251660 A1 | 10/2011 | Griswold |
| 2011/0251661 A1 | 10/2011 | Fifer |
| 2011/0251662 A1 | 10/2011 | Griswold et al. |
| 2011/0270339 A1 | 11/2011 | Murray, III et al. |
| 2011/0270340 A1 | 11/2011 | Pellegrini |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0108986 A1 | 5/2012 | Beasley et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1* | 7/2012 | Anderson ............ A61N 1/3756 600/347 |
| 2012/0172891 A1 | 7/2012 | Lee |
| 2012/0172892 A1 | 7/2012 | Grubac |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0110127 A1 | 5/2013 | Bornzin |
| 2013/0110219 A1 | 5/2013 | Bornzin et al. |
| 2013/0116738 A1 | 5/2013 | Samade |
| 2013/0116740 A1 | 5/2013 | Bornzin et al. |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |

(56) References Cited

U.S. PATENT DOCUMENTS

| | | |
|---|---|---|
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0107723 A1 | 4/2014 | Hou |
| 2014/0148815 A1 | 5/2014 | Wenzel et al. |
| 2014/0180306 A1 | 6/2014 | Grubac |
| 2015/0039069 A1 | 2/2015 | Rys et al. |
| 2015/0039070 A1 | 2/2015 | Kuhn |
| 2015/0039071 A1 | 2/2015 | Grubac |
| 2015/0051616 A1 | 2/2015 | Haasl |
| 2015/0051682 A1 | 2/2015 | Schmidt |
| 2015/0094668 A1 | 4/2015 | Wood |
| 2015/0352353 A1 | 12/2015 | Rys |
| 2016/0001068 A1 | 1/2016 | Grubac |
| 2016/0059002 A1 | 3/2016 | Grubac |
| 2016/0094668 A1 | 3/2016 | Chang et al. |
| 2017/0209688 A1 | 7/2017 | Drake et al. |
| 2020/0121923 A1 | 4/2020 | Kuhn et al. |
| 2020/0306522 A1 | 10/2020 | Chen et al. |

FOREIGN PATENT DOCUMENTS

| | | | |
|---|---|---|---|
| DE | 2053919 | A1 | 5/1972 |
| EP | 0212955 | A2 | 3/1987 |
| EP | 779080 | B1 | 5/2003 |
| JP | 0288666 | | 7/1990 |
| JP | 05245215 | A | 9/1993 |
| RU | 2011151104 | | 6/2013 |
| WO | 95/20993 | A2 | 8/1995 |
| WO | 0102053 | A1 | 1/2001 |
| WO | 03032807 | A1 | 4/2003 |
| WO | 2004028348 | A2 | 4/2004 |
| WO | 2009039400 | A1 | 3/2009 |
| WO | 2009042295 | A1 | 4/2009 |
| WO | 2010131157 | A1 | 11/2010 |
| WO | 2012092067 | A1 | 7/2012 |
| WO | 2012092074 | A1 | 7/2012 |
| WO | 2012135530 | A1 | 10/2012 |
| WO | 2014006471 | A1 | 1/2014 |
| WO | 2015017234 | A1 | 2/2015 |

OTHER PUBLICATIONS

Response to Office Action dated Nov. 26, 2018, from U.S. Appl. No. 16/128,270, filed Feb. 19, 2019, 31 pp.
http://www.mana-tech.com/factsheets/HomerMammalok.pdf.
Medtronic model SELECTSURE™ 3830 manual, 2013, 20 pages.
(PCT/US2017/014369) PCT Notification of Transmittal of the International Search Report and the Written Opinion of the International Searching Authority, dated May 10, 2017, 13 pages.
(PCT/US2017/014352) PCT Notification of Transmittal of the International Search Report and the Written Opinion of the International Searching Authority, or the Declaration, dated May 22, 2017, 8 pages.
(PCT/US2017/014361) PCT Notification of Transmittal of the International Search Report and the Written Opinion of the International Searching Authority, dated Apr. 3, 2017, 11 pages.
Advisory Action from U.S. Appl. No. 16/128,270, dated Jul. 12, 2019, 3 pp.
Notice of Allowance from U.S. Appl. No. 15/410,085, dated Jun. 26, 2019, 8 pp.
Response to Office Action dated Feb. 7, 2019, from U.S. Appl. No. 15/410,085, filed May 6, 2019, 13 pp.
Merriam-Webster Definition of "Compound Curve," accessed on Apr. 25, 2017, https://merriam-webster.com/dictionary/compound%20curve, 4 pp.
Spickler, et al., "Totally Self-Contained Intracardiac Pacemaker," J. Electrocardiology, vol. 3, Nos. 3 & 4, pp. 325-331, 1970. (Applicant points out, in accordance with MPEP 609.04(a), that the year of publication, 1970 is sufficiently eallier than the effective U.S. filing date, so that the particular month of publication is not in issue.).
Prosecution History from U.S. Appl. No. 13/955,393, dated from Nov. 26, 2014 through Aug. 10, 2018, 104 pp.
Notice of Allowance from U.S. Appl. No. 15/410,161, dated Jun. 13, 2018, 5 pp.
Non-Final Office Action from U.S. Appl. No. 16/128,270, dated Nov. 26, 2018, 8 pp.
U.S. Appl. No. 16/128,270, filed by Jonathan L. Kuhn et al., filed Sep. 11, 2018.
(PCT/US2017/01435) PCT Invitation to Pay Additional Fees and, Where Applicable, Protest Fee, dated Apr. 3, 2017, 3 pages.
Response to Final Office Action dated Apr. 29, 2019, from U.S. Appl. No. 16/128,270, filed Sep. 11, 2018, 13 pp.
U.S. Appl. No. 62/825,233, filed by Xin Chen et al., filed Mar. 28, 2019.
Notice of Allowance from U.S. Appl. No. 16/128,270, dated Aug. 21, 2019, 8 pp.
International Search Report and Written Opinion of International Application No. PCT/US2020/024582, dated Jul. 7, 2020, 8 pp.
U.S. Appl. No. 16/825,143, filed by Chen et al., filed Mar. 20, 2020.
Amendment in Response to Office Action dated Feb. 7, 2019, from U.S. Appl. No. 15/410,085, filed May 6, 2019, 13 pp.
Final Office Action from U.S. Appl. No. 16/128,270, dated Apr. 29, 2019, 10 pp.
(PCT/US2017/014352) PCT Invitation to Pay Additional Fees and, Where Applicable, Protest Fee, dated Apr. 3, 2017, 7 pages.
Prosecution History from U.S. Appl. No. 16/128,270, dated Nov. 26, 2018 through Aug. 21, 2019, 56 pp.

* cited by examiner

INTERVENTIONAL MEDICAL DEVICES, DEVICE SYSTEMS, AND FIXATION COMPONENTS THEREOF

CROSS-REFERENCE TO RELATED APPLICATIONS

This application is a Continuation of U.S. patent application Ser. No. 15/410,161, filed Jan. 19, 2017, entitled "INTERVENTIONAL MEDICAL DEVICES, DEVICE SYSTEMS, AND FIXATION COMPONENTS THEREOF", which claims the benefit of the filing date of Provisional U.S. Patent Application No. 62/281,403, filed Jan. 21, 2016, entitled "INTERVENTIONAL MEDICAL DEVICES AND FIXATION COMPONENTS THEREOF", the content of both of which are incorporated by reference in their entirety.

FIELD OF THE DISCLOSURE

The present disclosure pertains to medical device systems, and, more particularly, to relatively compact implantable medical devices thereof and associated fixation components.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic that shows a potential cardiac implant site for such a device within an appendage 102 of a right atrium RA. An implanting physician may employ a delivery tool 400 to deploy a relatively compact medical device to the site, for example, after maneuvering tool 400, with the device loaded therein, up through the inferior vena cava IVC and into the right atrium RA.

BRIEF SUMMARY

Embodiments of medical device systems disclosed herein include an implantable medical device and a delivery tool, wherein the device has a fixation mechanism formed by a plurality of tines fixedly mounted and spaced from one another around a perimeter of a distal end of the device, and the tool includes a tubular sidewall that defines a lumen into which the device may be loaded, the lumen having a distal opening through which the device may be deployed. In some embodiments, each tine of the device fixation mechanism includes: a first segment fixedly attached to the device and extending therefrom; a second segment extending from the first segment; and a third segment, to which the second segment extends, the third segment having a rounded free distal end spaced from the perimeter of the device housing distal end; and wherein: the first segment has a spring-biased pre-formed curvature, extending distally from the device distal end, and then sweeping laterally outward from the axis of the device and then proximally to the second segment; the second segment is pre-formed to extend proximally along a relatively straight line to the third segment, the relatively straight line of the second segment being oriented, by the spring-biased preformed curvature of the first segment, to intersect the axis of the device at an acute angle of between about 30 degrees and about 50 degrees; the third segment has a deformable pre-formed curvature that extends back toward the axis of the device such that, when the curvature of the third segment is un-deformed, the second and third segments enclose an angle in a range from about 70 degrees to about 120 degrees; and the tines are each configured such that when the device is loaded in the lumen of the tool and the rounded free distal end of the third segment of each tine engages the delivery tool sidewall to hold the tines in a spring-loaded condition, the first segment of each tine becomes relatively straightened, and the third segment of each tine extends away from the axis of the device at an acute angle in a range from about 45 degrees to about 75 degrees.

According to some embodiments, the aforementioned tines are part of a tissue penetrating fixation component that also includes a base configured to be fixedly attached to the device so that a perimeter of the component extends around an electrode of the device, and so that a longitudinal axis of the component is generally aligned along that of the device. The plurality of tines extend from the base, and each tine includes: a proximal, spring portion (corresponding to the aforementioned first segment) being fixedly attached to the base and having a spring-biased pre-formed curvature, the pre-formed curvature, in proximity to the base, extending in a first direction, generally parallel to the axis of the component, and then sweeping laterally, outward from the axis; and a distal portion (corresponding to the aforementioned second and third segments) including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis at an acute angle of between about 30 degrees and about 50 degrees, the hook section having a deformable preformed curvature that extends from the proximal section back toward the axis of the component, the tip section being pre-formed to extend along a relatively straight line from the hook section to the rounded free distal end, and the tip section being oriented by the pre-formed curvature of the hook section, when un-deformed, to extend toward the axis of the component, such that the tip section and the proximal section enclose an angle in a range from about 70 degrees to about 120 degrees; and wherein: when the device, having the fixation component fixedly attached thereto, is loaded within a tubular sidewall of a delivery tool, so that the rounded free distal end of each tine of the component engages an inner surface of the sidewall in proximity to a distal opening of the tool, to hold the proximal, spring portion of each tine of the component in a spring-loaded condition, each tip section of the distal portion extends away from the axis of the component at an acute angle in a range from about 45 degrees to about 75 degrees for deployment of the corresponding rounded free distal end out from the distal opening of the tool tubular sidewall; and upon deployment of the rounded free distal end of each tine, the tip section of each distal portion rotates away from the axis to approach an angle of 90 degrees, relative to the axis, in response to an initial release of the spring-loaded condition of the corresponding proximal, spring portion.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
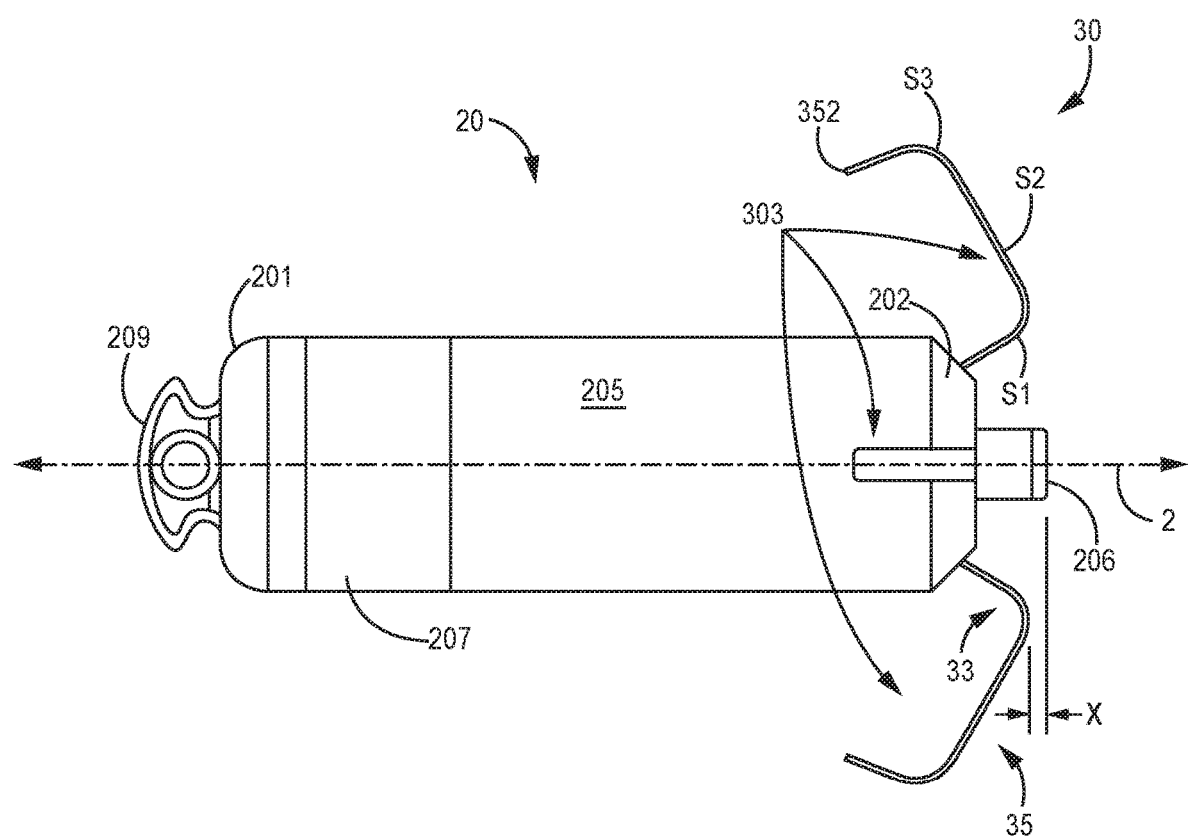
FIG. 2A is a plan view of a relatively compact implantable medical device, according to some embodiments.

FIG. 2A is a plan view of a relatively compact implantable medical device 20, according to some embodiments. FIG. 2A illustrates device 20 including a hermetically sealed housing 205, preferably formed from a biocompatible and biostable metal such as titanium, which contains a pulse generator (e.g., a power source and an electronic controller—not shown), a fixation mechanism 30, and an electrode 206, which is spaced apart from a distal end 202 of housing 205, for example, being coupled to the pulse generator by a conductor of an hermetic feedthrough assembly (not shown) that is constructed according to methods known to those skilled in the art of implantable medical devices. FIG. 2A further illustrates device 20 including a holding member 209 mounted to a proximal end 201 of housing 205, wherein holding member 209 is configured for temporarily tethering device 20 to a delivery tool, such as tool 400, according to methods known in the art.

Housing 205 may be overlaid with an insulative layer, for example, medical grade polyurethane, parylene, or silicone, and, with further reference to FIG. 2A, another electrode 207 of device 20 may be formed by removing a portion of the insulative layer to expose the metallic surface of housing 205. According to the illustrated embodiment, electrode 206 may function in conjunction with electrode 207 for bipolar pacing and sensing, when elastically deformable tines 303 of fixation mechanism 30 hold electrode 206 in intimate tissue contact at a target implant site, for example, within right atrial appendage 102 as illustrated schematically in FIG. 2B.

In FIG. 2A, one of tines 303 is shown divided into first, second, and third segments S1, S2, S3, each of which is pre-formed into, and elastically deformable from, the illustrated shape thereof. According to the illustrated embodiment, first segment S1 is fixedly attached to distal end 202 of device housing 205 and extends around a pre-formed curvature to second segment S2, which extends proximally along a relatively straight line to third segment S3. FIG. 2A illustrates third segment S3 extending around a pre-formed curvature to a free distal end 352 of tine 303.

Figure 1:
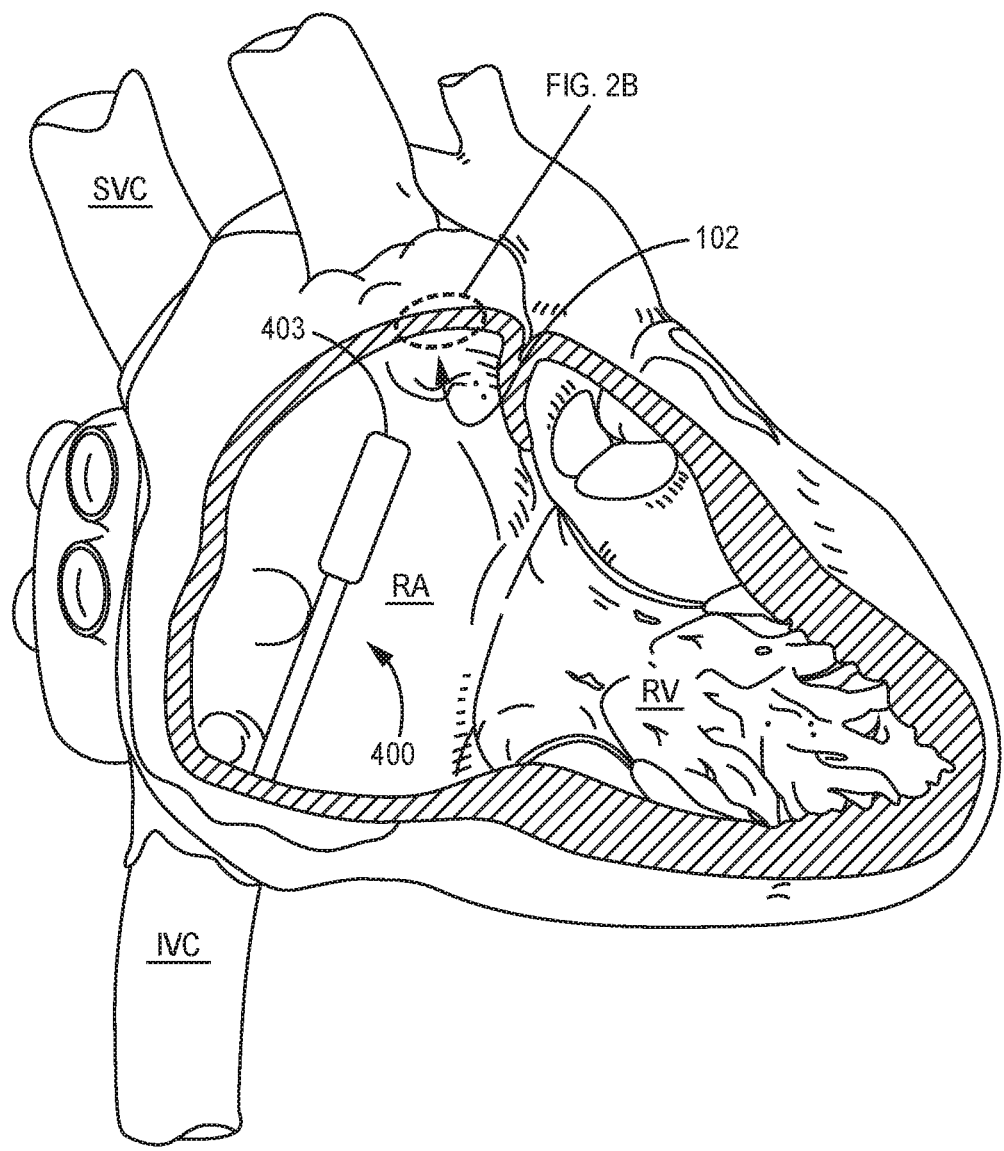
FIG. 1 is a schematic diagram showing an exemplary cardiac implant site for which embodiments of the present invention are particularly suited.
Figure 2B:
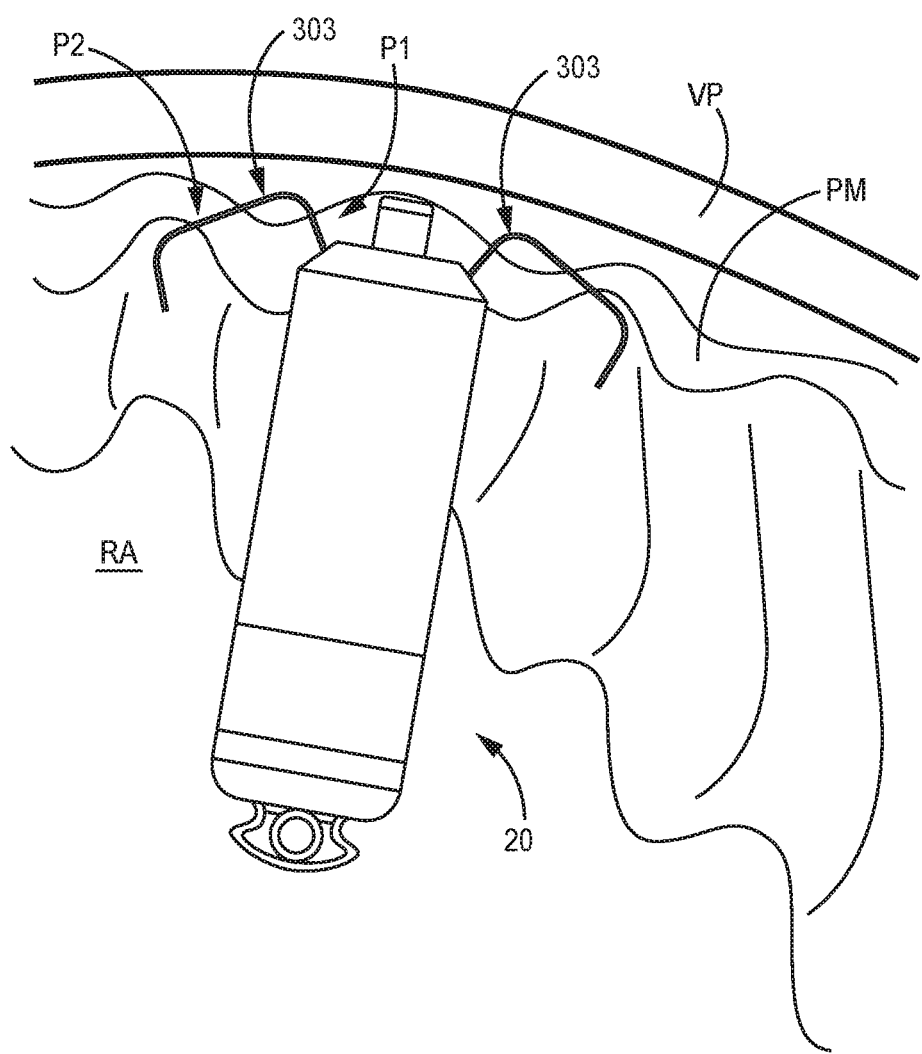
FIG. 2B is a schematic section showing the device of FIG. 2A implanted, according to some embodiments and methods.

FIG. 2B is a schematic section showing device 20 implanted in right atrium RA (FIG. 1), according to some embodiments and methods. With reference to FIG. 2B, a portion the right atrial wall, for example, in appendage 102, is shown having a laminate structure that includes an inner layer of pectinate muscle PM and an outer layer of visceral pericardium VP, which forms the epicardial surface. FIG. 2B illustrates device 20 secured at the implant site by tines 303 of fixation mechanism 30 penetrating through the layer of pectinate muscle PM without perforating through visceral pericardium VP, which could result in pericardial effusion. Tines 303 of mechanism 30, according to embodiments disclosed herein, are configured for spring-loaded release, upon deployment out through a distal opening 403 of a lumen 435 of delivery tool 400, as described below in conjunction with FIGS. 4 and 5B-C, so that tine free distal end 352 penetrates pectinate muscle PM without perforating visceral pericardium VP. It should be noted that alternate suitable implant sites for embodiments of fixation member tines described herein can be along any endocardial surface defined by pectinate muscle PM.

Figure 3A:
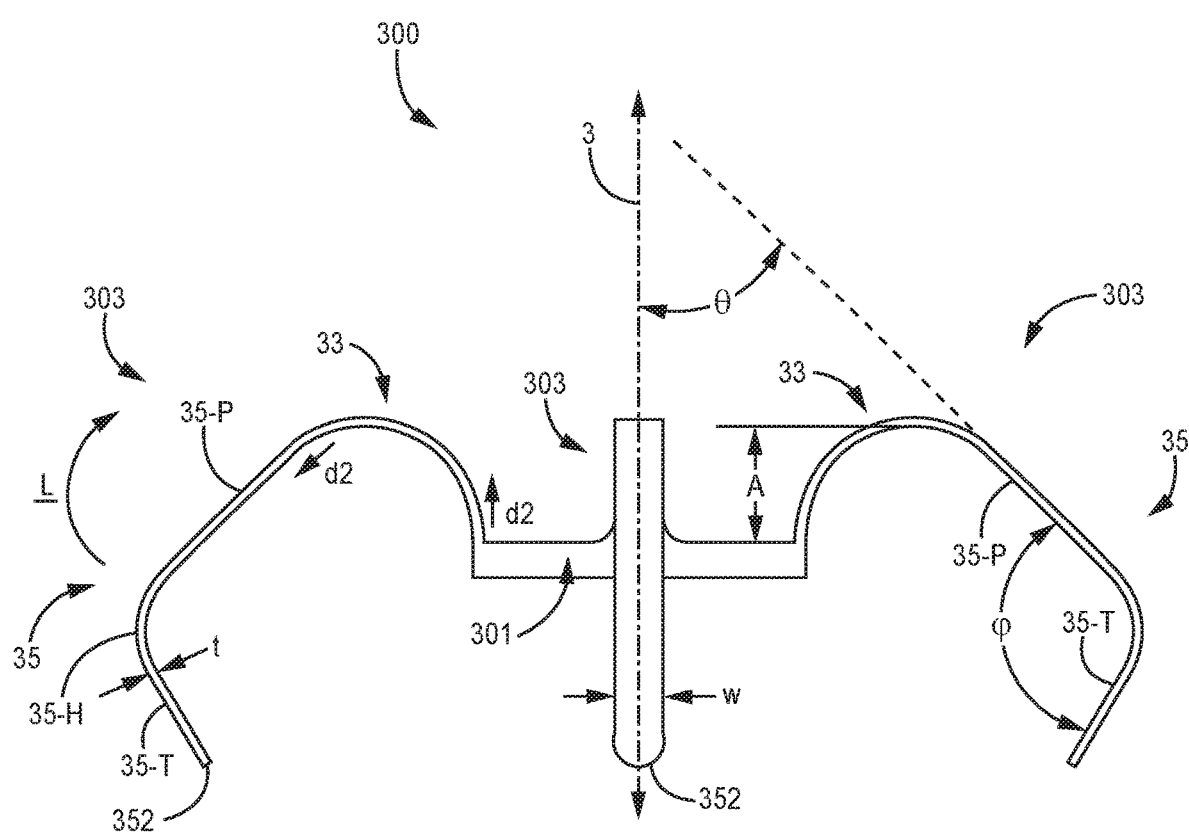
FIG. 3A is an elevation view of an exemplary fixation component which may be employed by the device of FIG. 2A, according to some embodiments.
Figure 3B:
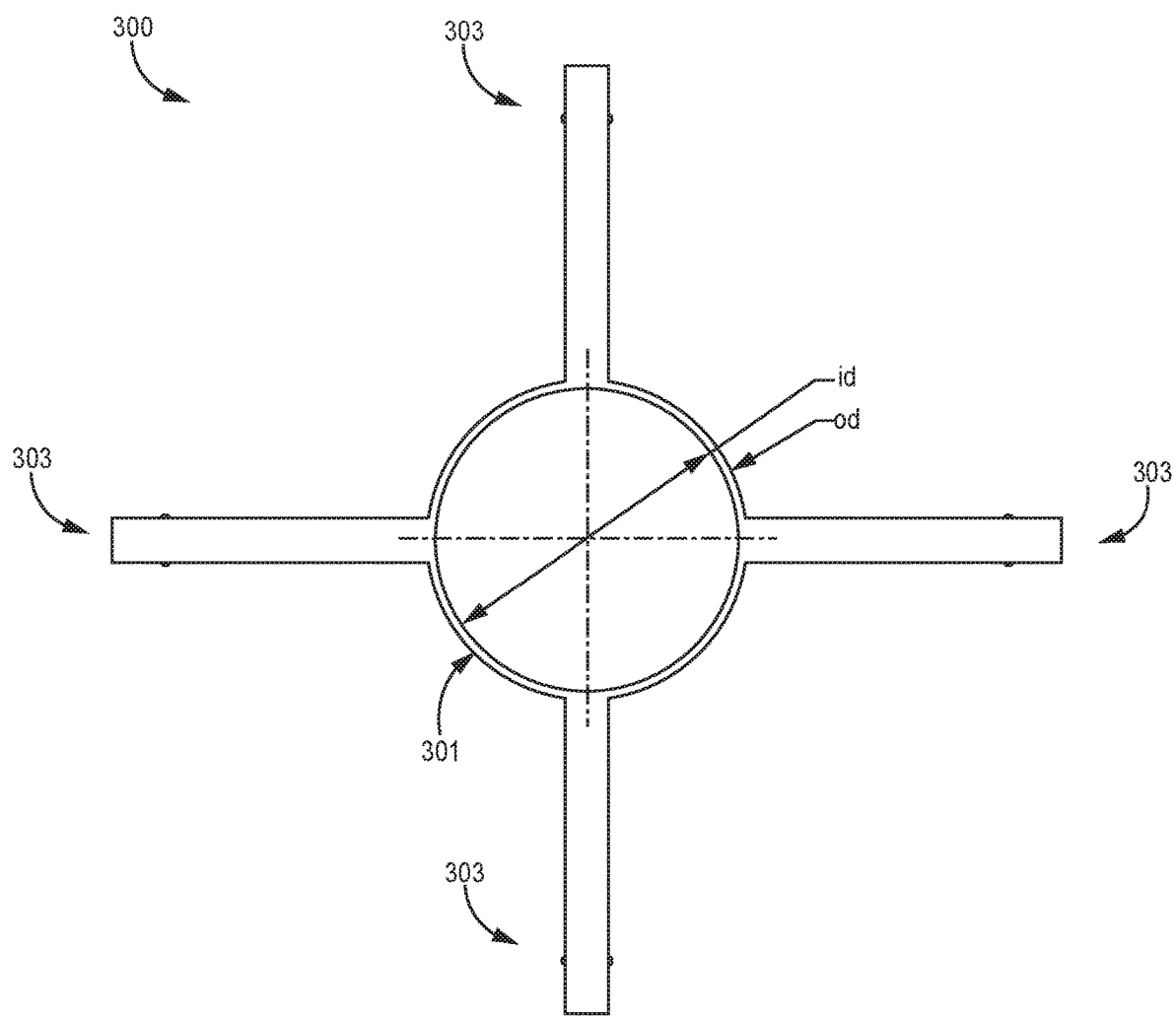
FIG. 3B is an end view of the component of FIG. 3A, according to some embodiments.

FIGS. 3A-B are elevation and end views of a fixation component 300 that forms fixation mechanism 30, according to some embodiments. FIGS. 3A-B illustrate component 300 including a base 301 from which a plurality of tines 303 extend, being spaced apart from one another around a perimeter of base 301. Tines 303 are shown in a relaxed, or pre-formed spring-biased condition. In FIG. 3A, a longitudinal axis 3 of component 300 is shown being defined by base 301 such that, when base 301 is mounted around distal end 202 of device housing 205, and a perimeter of component 300 extends around electrode 206, axis 3 is generally aligned along longitudinal axis 2 of device 20 (FIG. 2A). With reference to FIG. 3B, base 301 may have an inner diameter id of about 0.20 inch and an outer diameter od of about 0.21 inch. Fixation component 300 may be mounted to distal end 202 of device housing 205, for example, in a manner similar to that described for a fixation component 102 in co-pending and commonly assigned United States Patent Application 2012/0172690 (filed on Oct. 28, 2011), which description is hereby incorporated by reference. However, according to some alternate embodiments, fixation mechanism 30 may be separately formed tines 303 (not integrated together with base 301) that are individually mounted to distal end 202 of device housing 205.

Tines 303 are preferably formed from a super-elastic material, for example, a Nickel-Titanium alloy (Nitinol). Fixation component 300 may be cut from a medical grade Nitinol tubing that conforms to the chemical, physical, mechanical, and metallurgical requirements of the ASTM F2063 standard, and has a wall thickness of about 0.005 inch. In this case, tines 303 are integrally formed with base 301 and each tine 303 may have a constant thickness t of 0.005 inch±0.001 inch. After cutting the tubing, tines 303 are shaped into the configuration shown in FIG. 3A by bending and holding tines 303, while heat treating according to methods known to those skilled in the art.

FIG. 3A illustrates each tine 303 including a proximal, spring portion 33, which corresponds to first segment S1 of FIG. 2A, and a distal portion 35, which corresponds to second and third segments S2, S3 of FIG. 2A, and which is terminated by free distal end 352. Free distal end 352 is preferably rounded, as shown in FIG. 3A. FIG. 3A further illustrates distal portion 35 including a proximal section 35-P, a hook section 35-H, and a tip section 35-T. The shaped configuration and width of each tine 303, along with the super-elastic stiffness properties of Nitinol, provide a sufficient spring force and structural stiffness for tines 303 to engage tissue for the fixation of device 20 at an implant site when deployed by delivery tool 400, as described in greater detail below. With reference to FIG. 3A, each tine 303 has a width w which is preferably no less than about 0.02 inch, for example, being in a range from about 0.025 inch to about 0.032 inch. Such a width provides the aforementioned structural stiffness, as well as a radiopaque density that facilitates fluoroscopic visualization during and after the implant procedure.

With further reference to FIG. 3A, according to the illustrated embodiment, each proximal, spring portion 33 is fixedly attached to base 301 and has a spring-biased pre-formed curvature, which, in proximity to the base, extends in a first direction d1, generally parallel to axis 3, and then sweeps laterally, outward from axis 3 to distal portion proximal section 35-P. Distal portion proximal section 35-P, according to the illustrate embodiment, is pre-formed to extend in a second direction d2 and along a relatively straight line (dashed line), being oriented, by the spring-biased pre-formed curvature of proximal, spring portion 33, so that second direction d2 is generally opposite first direction d1, and the relatively straight line intersects axis 3 at an acute angle θ. According to some embodiments, angle θ is between about 30 degrees and about 50 degrees. In an exemplary embodiment of component 300, to be employed by an exemplary embodiment of device 20 that has housing 205 sized to an outer diameter of about 0.26 inch (20 French), the spring-biased pre-formed curvature of each proximal, spring portion 33 is defined by a single radius of 0.067 inch±0.010 inch; a distance A between base 301 and each intersection of proximal, spring portion 33 and distal portion proximal segment 35-P is 0.092 inch±0.005 inch; a length of each distal portion proximal segment 35-P is 0.100 inch±0.005 inch; and angle θ is about 45 degrees.

With further reference to FIG. 3A, each distal portion hook section 35-H has a deformable pre-formed curvature that extends from proximal, spring portion 33 back toward axis 3. FIG. 3A further illustrates tip section 35-T of distal portion 35 extending from hook section 35-T along a relatively straight line to rounded free distal end 352. Tip section 35-T is shown oriented by the pre-formed curvature of hook section 35-H, when un-deformed, to extend toward axis 3, such that tip section 35-T and proximal section 35-P are shown enclosing an angle φ, which, according to the illustrated embodiment, is no less than about 90 degrees, but can be up to about 120 degrees. In the aforementioned exemplary embodiment of component 300, the deformable pre-formed curvature of each hook section 35-H, when un-deformed, is defined by a single radius of about 0.05 inch; and a length of each tip section 35-T is 0.064 inch±0.005 inch.

Figure 3C:
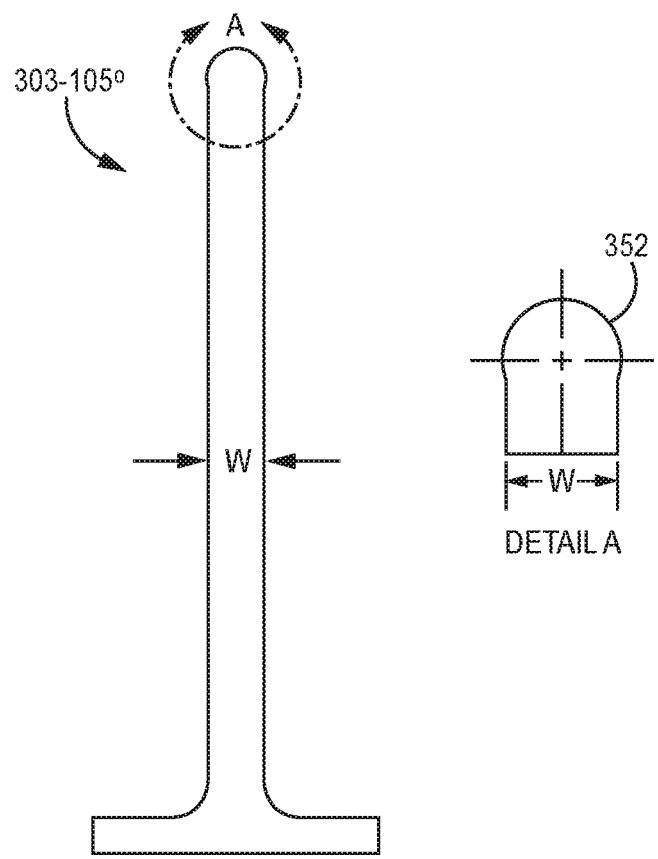
FIG. 3C is a plan view of a portion of the component of FIGS. 3A-B, prior to forming, according to some embodiments.
Figure 3D:
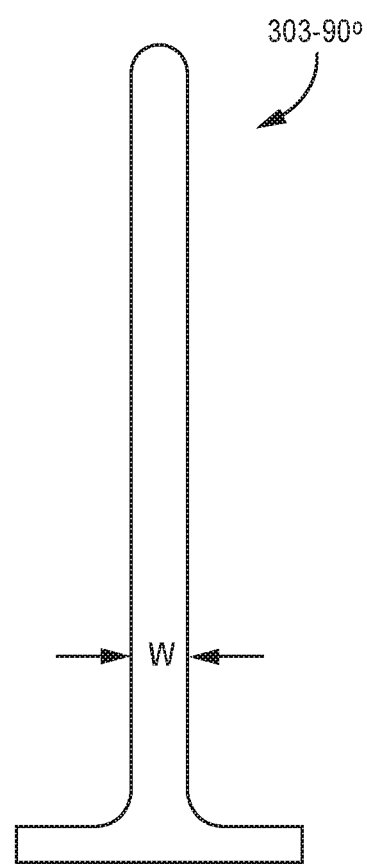
FIG. 3D is a plan view of a portion of the component of FIGS. 3A-B, prior to forming, according to some alternate embodiments.

FIGS. 3C-D are plan views of alternate tine embodiments prior to being formed into the configuration of FIG. 3A, wherein tine 303—105° of FIG. 3C is suitable for an exemplary component 300 in which angle φ is about 105 degrees, and wherein tine 303—90° of FIG. 3D is suitable for an exemplary component 300 in which angle φ is about 90 degrees. With further reference to FIGS. 3C-D, an exemplary width w of each tine 303 is 0.028 inch±0.001 inch, and, in the tine embodiment of FIG. 3C, rounded free distal end 352 of tine 303—105° has an enlarged width defined by a diameter of 0.030 inch±0.001 inch.

Figure 4:
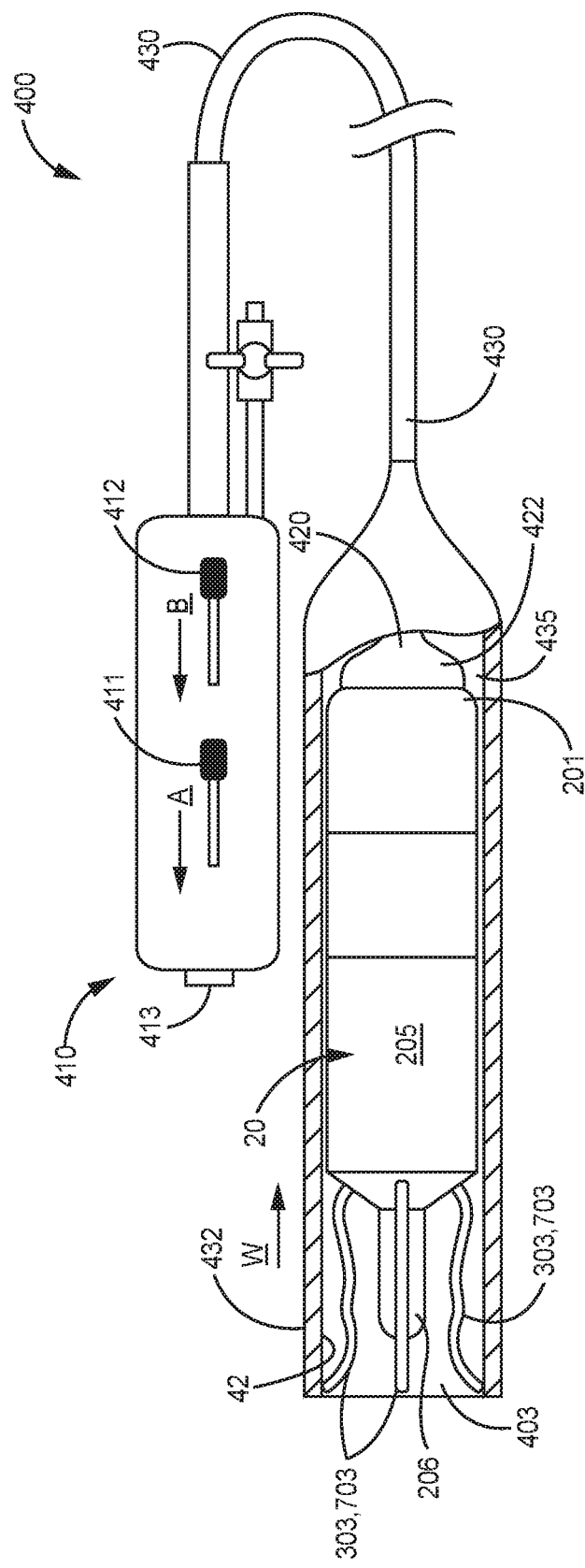
FIG. 4 is a plan view of a medical device system with a partial cut-away section, according to some embodiments.

FIG. 4 is a plan view of medical device system with a partial cut-away section, according to some embodiments, wherein the system includes device 20 and a delivery tool 400, in which device 20 is loaded for deployment to a target implant site. FIG. 4 illustrates tool 400 including a handle 410, an elongate outer member 430, and an elongate inner member 420 that extends within lumen 435 of outer member 430. FIG. 4 further illustrates inner member 420 including a distal end 422, which is configured to engage implantable medical device 20 by abutting proximal end 201 of device housing 205, as shown in the cut-away section. An entirety of device 20 is shown loaded within a tubular sidewall 432 that defines a distal portion of outer member lumen 435, for example, having been loaded therein by pulling device 20, with housing proximal end 201 leading, in through lumen distal opening 403. According to the illustrated embodiment, an inner surface 42 of tubular sidewall 432 engages tines 303 (or 703 as described below in conjunction with FIG. 6A), as device 20 is loaded into lumen 435, to deform tines 303, per arrow L of FIG. 3A, and then to hold each tine 303 of the loaded device 20 in a spring-loaded condition, which is described below in conjunction with FIG. 5A. According to the above-described exemplary embodiments of fixation component 300, with device housing 205 sized to an outer diameter of about 0.26 inch (20 French), a diameter of lumen 435, defined by inner surface 42, is about 0.28 inch (21 French).

With further reference to FIG. 4, a proximal end of outer member 430 is coupled to a control member 412 of handle 410 such that an entirety of outer member 430 is movable with respect to inner member 420, via control member 412, for example, so that an operator may retract outer member 430, per arrow W, relative to device 20 and inner member 420, to deploy device 20 out through distal opening 403, after positioning the system in proximity to a target implant site. The operator may position the system by advancing tool 400 through a venous system of the patient, for example, from a femoral venous access site and up through the inferior vena cava IVC (FIG. 1). Delivery tool 400 may include articulating features to facilitate the navigation of the distal portion of delivery tool 400. For example, inner member 420 of delivery tool 400 may include a pull wire assembly (not shown) integrated therein and being coupled to another control member 411 of handle 410 that, when moved per arrow A, causes inner member 420 and outer member 430 to bend along distal portions thereof. A length of outer member 430, between handle 410 and distal opening 403, when outer member 430 is in the position shown in FIG. 4, may be between about 103 cm and about 107 cm, for example, to reach into the right atrium RA from the femoral access site. Suitable construction detail for a delivery tool like tool 400 is described in co-pending and commonly assigned U.S. Patent Application 2015/0094668, Ser. No. 14/039,937 (filed on Sep. 27, 2013), the description of which is hereby incorporated by reference.

Figure 5A:
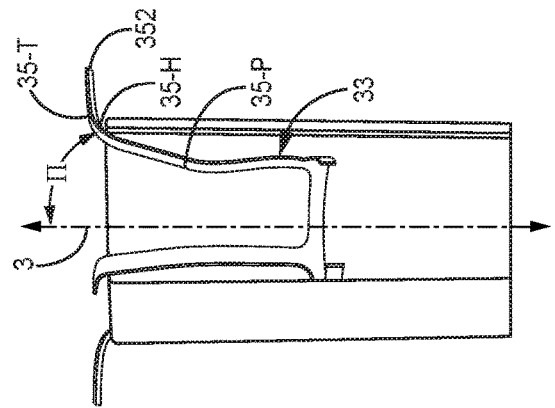
FIG. 5A is a schematic showing a spring loaded condition of the fixation component of the atrial portion of the device, according to some embodiments.
Figure 5B:
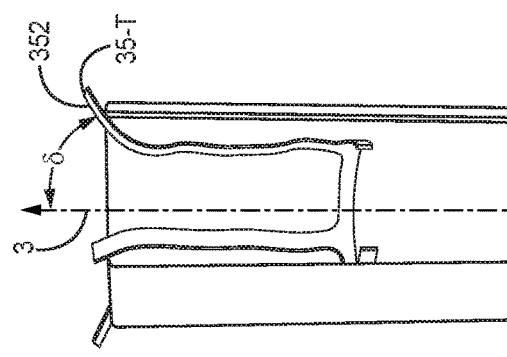
FIG. 5B is a schematic showing an initial release of the fixation component from the spring loading shown in FIG. 5A.
Figure 5C:
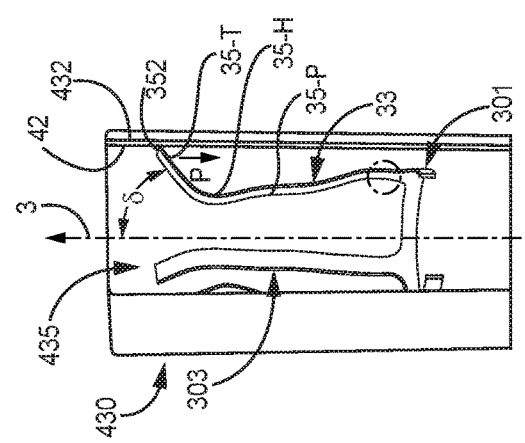
FIG. 5C is a schematic showing rotation for initial penetration of the fixation component after the initial release of FIG. 5B.
Figure 5D:
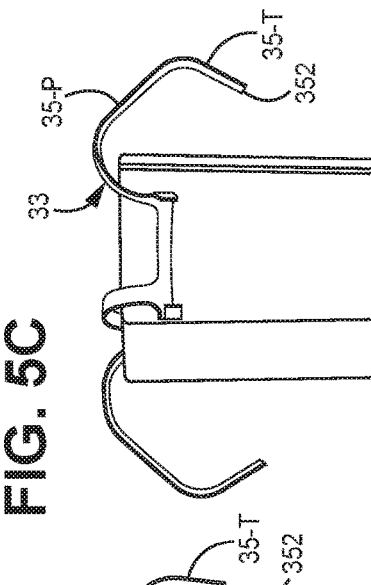
FIG. 5D is a schematic showing fixation component movement, subsequent to initial penetration.
Figure 5E:
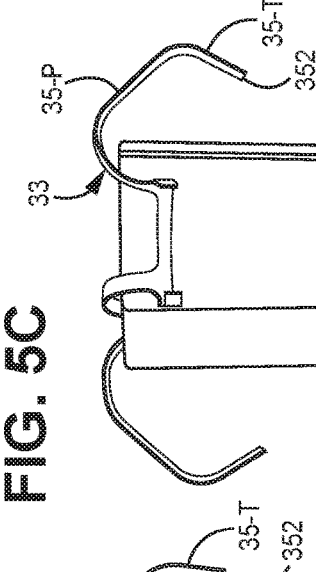
FIG. 5E is a schematic showing fixation component movement, subsequent to penetration.
Figure 5F:
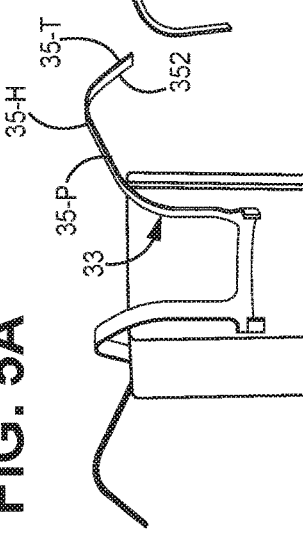
FIG. 5F is a schematic showing fixation component movement, subsequent to penetration.

According to some methods, once the operator has advanced the system of FIG. 4 into atrial appendage 102 (FIG. 1), so that distal opening 403 abuts pectinate muscle PM therein (FIG. 2B) at the target implant site, the operator can move control member 412, per arrow B, to retract outer member 430 relative to device 20 and thereby release the spring loading of fixation component 300 so that tines 303 engage with pectinate muscle PM to secure device 20 at the implant site, as illustrated in FIG. 2B. However, it should be noted that, according to alternative embodiments and methods, delivery tool 400 may be configured so that an operator can advance inner member 420 relative to outer member 430 to push device 20 out through distal opening 403 for deployment. FIGS. 5A-F are schematics outlining a sequence of events corresponding to the release of above-described embodiments of fixation tines 303. (Although the schematics show tines 303 integrally formed with base 301, as in above-described embodiments of component 300, it should be understood that the sequence of events in FIGS. 5A-F may also apply to alternate embodiments in which tines 303 are not integrally formed with base 301.) FIG. 5A illustrates a maximum deformation of tines 303 when held in the spring-loaded condition by the engagement of rounded free distal end 352 with inner surface 42 of outer member tubular sidewall 432, wherein proximal, spring portion 33 becomes relatively straightened, and a location of the maximum principle strain along each tine 303 is in relatively close proximity to base 301 (designated by dashed-line circle). With reference back to FIG. 3A, the aforementioned exemplary length of distal portion tip section 35-T and the aforementioned associated angle φ (no less than 90 degrees) help to keep the deformed tines 303 from touching one another within lumen 435 and to prevent free distal ends 352 from being pulled proximally, per arrow P, when outer member 430 is retracted to release the spring loading of tines 303. FIG. 5A further illustrates tip section 35-T extending away from axis 3 at an acute angle δ, which is preferably in a range from about 45 degrees to about 75 degrees for an initial release of the spring loading of each tine 303, upon retraction of outer member 430, as depicted in FIG. 5B. With reference to FIG. 5C, once free distal end 352 is released from engagement with inner surface 42 for deployment into tissue at the implant site, the spring force of proximal, spring portion 33 and the pre-formed curvature of distal portion hook section 35-T cause distal portion tip section 35-T to immediately rotate away from axis 3 to an angle π, which approaches 90 degrees, so that tip section 35-T is oriented approximately normal to axis 3 for initial penetration of pectinate muscle PM. Thus each tine free distal end 352 is deployed in a direction toward pectinate muscle PM that ultimately prevents tines 303 from perforating the underlying visceral pericardium VP (reference FIG. 2B). FIGS. 5D-F illustrates the subsequent movement of tines 303, being driven by the release of proximal, spring portion 33 from the spring loading. According to the illustrated embodiment, this release of proximal, spring portion 33 causes free distal end 352, after penetrating through pectinate muscle PM in a first direction, at a first location P1, to penetrate back through in an opposite direction, at a second location P2, so that device 20 may be securely fixed at the implant site, as illustrated in FIG. 2B.

The configuration of tine distal portion 35, for example, embodied by the aforementioned exemplary lengths of proximal section 35-P and tip section 35-T, and the pre-formed curvature of hook section 35-H, provide a structural stiffness and reach to each tine 303 that is sufficient for deformation and subsequent penetration of free distal end 352 through pectinate muscle PM, as shown in FIG. 2B, but is not sufficient for penetration through visceral pericardium VP. Even if the operator ends up advancing the system into appendage 102 so that distal opening 403 of tool 400 abuts visceral pericardium VP, between folds of pectinate muscle PM, free distal end 352, according to this configuration of tines 303, is not backed-up by sufficient stiffness to penetrate through visceral pericardium VP, so tip section 35-T of tine distal portion 35 is redirected, laterally, toward pectinate muscle PM.

It should be noted that an operator may employ tines 303 to secure device 20 in atrial appendage 102 in an alternative fashion, wherein tines 303 are fully released from the spring-loaded condition without engaging any tissue (FIG. 5F), and then device 20 is advanced to the implant site so that tines 303 wedge between opposing surfaces of pectinate muscle PM within atrial appendage 102 to secure device 20 in place.

With reference back to FIGS. 2A-B, according to some preferred embodiments, for example, in order to assure intimate contact of electrode 206 with tissue, when fixation tines 303 secure device 20 at a target implant site, electrode 206 is spaced distally apart from device housing distal end 202 by a distance along longitudinal axis 2. Electrode 206 may be approximately flush with an intersection between proximal, spring portion 33 and distal portion 35, or spaced distally apart from the intersection by a distance X that may be up to about 2 mm, as depicted in FIG. 2A.

Figure 6A:
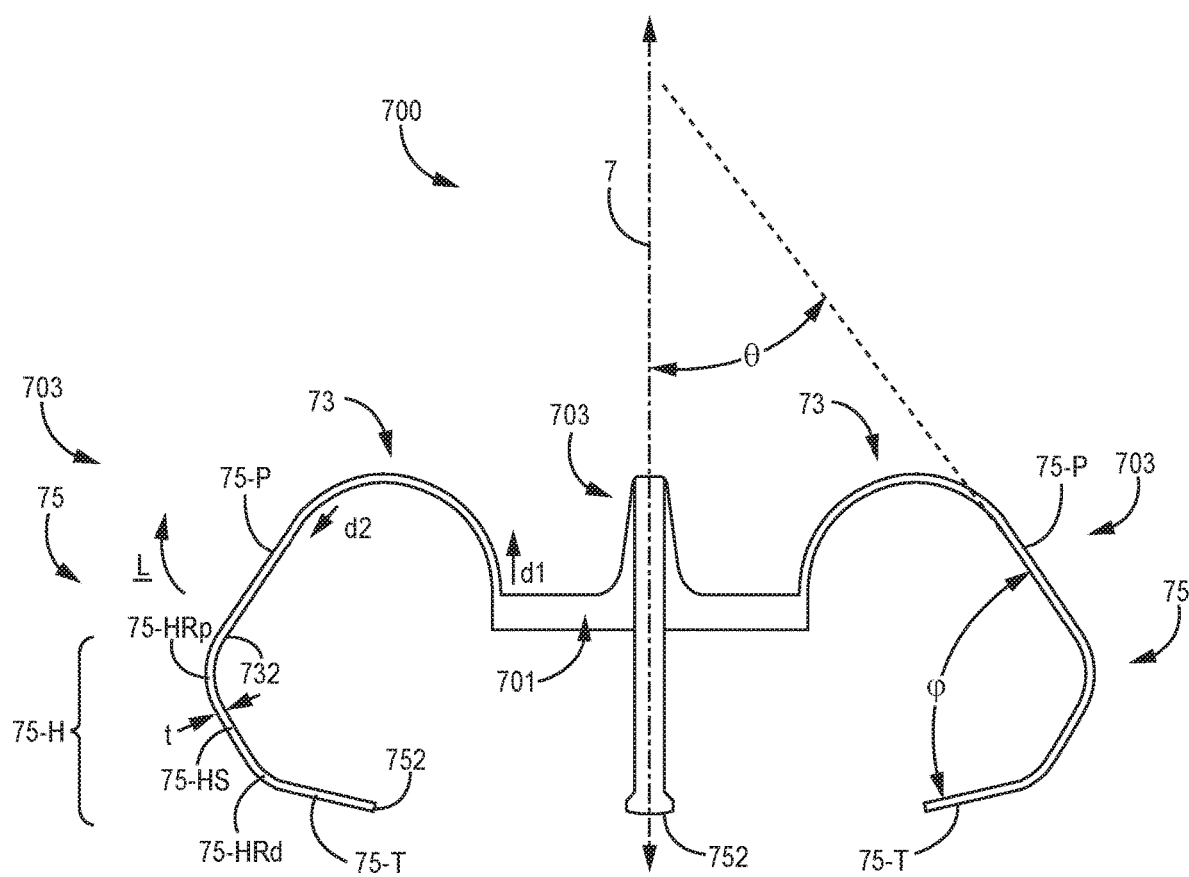
FIG. 6A is an elevation view of an exemplary fixation component which may be employed by the device of FIG. 2A, according to some additional embodiments.
Figure 6B:
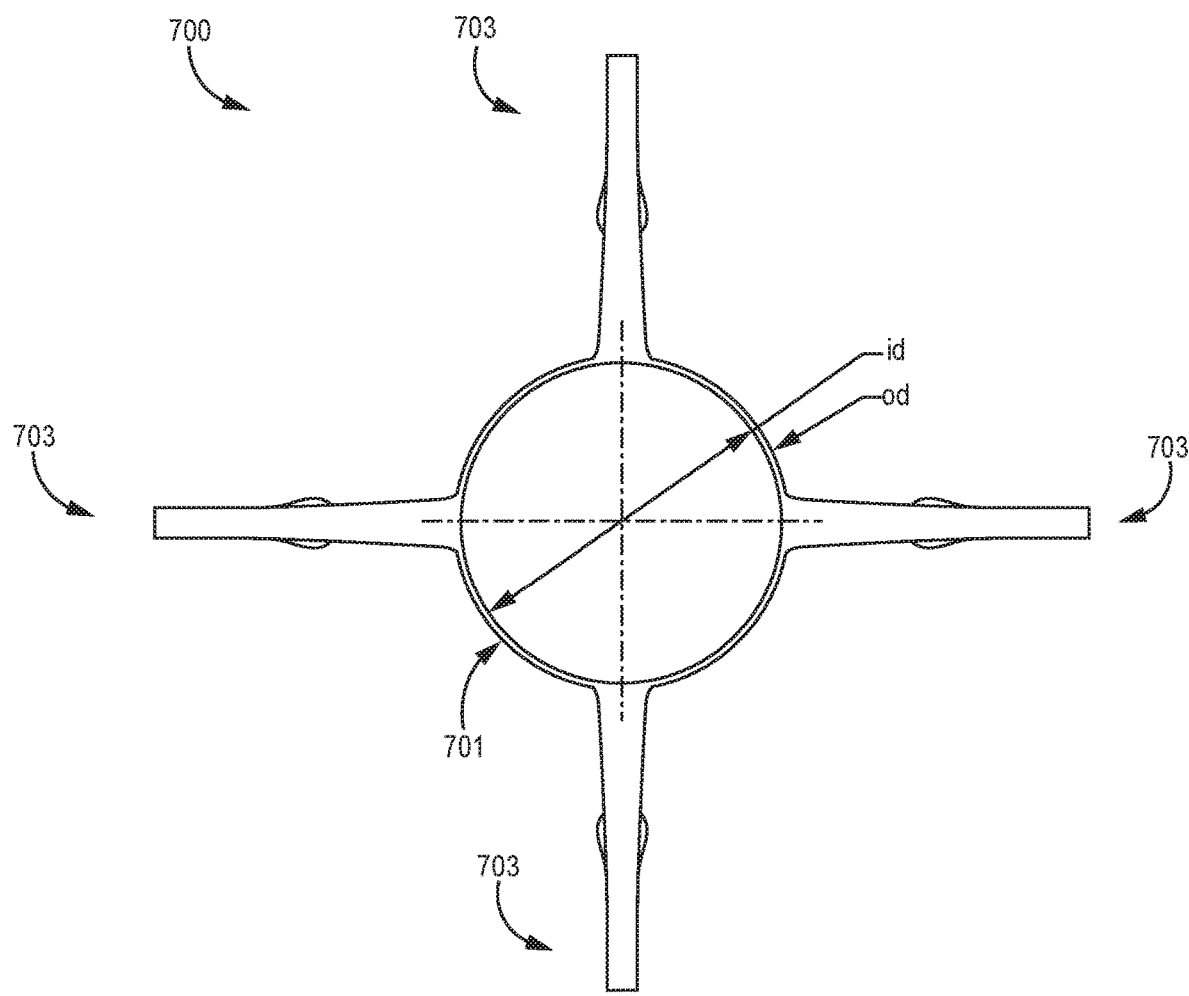
FIG. 6B is an end view of the component of FIG. 6A, according to some additional embodiments.

FIG. 6A-B are elevation and end views of an exemplary fixation component 700 which may be employed by device 20, according to some additional embodiments. FIGS. 6A-B illustrate component 700 including a base 701 from which a plurality of tines 703 extend, being spaced apart from one another around a perimeter of base 701. In FIG. 6A, a longitudinal axis 7 of component 700 is shown being defined by base 701 such that, when base 701 is mounted around distal end 202 of device housing 205, so that a perimeter of component 700 extends around electrode 206, axis 7 is generally aligned along longitudinal axis 2 of device 20

(FIG. 2A). With reference to FIG. 6B, base 701 may have an inner diameter id of about 0.20 inch and an outer diameter od of about 0.21 inch.

Like component 300, component 700 may be cut from the aforementioned medical grade Nitinol tubing, and each tine 703, integrally formed with base 701, may have a constant thickness t of 0.005 inch±0.001 inch. After cutting the tubing, tines 703 are shaped into the configuration shown in FIG. 6A by bending and holding tines 703, while heat treating according to methods known to those skilled in the art. FIG. 6A illustrates each tine 703 including a proximal, spring portion 73 and distal portion 75, which is terminated by a rounded free distal end 752, wherein both portions 73, 75 are pre-formed into, and elastically deformable from the illustrated shape. The shaped configuration and width of each tine 703, along with the super-elastic stiffness properties of Nitinol, provide a sufficient spring force and structural stiffness for tines 703 to engage tissue for the fixation of device 20 at an implant site when deployed by delivery tool 400, as described above for component 300. Furthermore, each tine 703, when device 20 is loaded in delivery tool 400, becomes deformed as generally shown in FIG. 4.

According to the illustrated embodiment, each proximal, spring portion 73 is fixedly attached to base 701 and has a spring-biased pre-formed curvature, which, in proximity to the base, extends in a first direction d1, generally parallel to axis 7, and then sweeps laterally, outward from axis 7 to a proximal section 73-P of distal portion 75. Proximal section 73-P is shown pre-formed to extend in a second direction d2 and along a relatively straight line (dashed line), being oriented, by the spring-biased pre-formed curvature of proximal, spring portion 73, so that second direction d2 is generally opposite first direction d1, and the relatively straight line intersects axis 7 at acute angle θ, which, according to some embodiments, is between about 30 degrees and about 50 degrees. In an exemplary embodiment of component 700, to be employed by an exemplary embodiment of device 20 that has housing 205 sized to an outer diameter of about 0.26 inch (20 French), the spring-biased pre-formed curvature of each proximal, spring portion 73 is defined by a single radius of 0.067 inch±0.010 inch; a distance A between base 701 and each intersection of proximal, spring portion 73 and distal portion proximal segment 75-P is 0.092 inch±0.005 inch; a length of each spring segment distal segment 73-D is 0.085 inch±0.005 inch; and angle θ is about 34 degrees.

With further reference to FIG. 6A, each distal portion 75 further includes a hook section 75-H, which has a deformable pre-formed curvature extending from distal proximal, spring portion 73 back toward axis 7, and a tip section 75-T, which is pre-formed to extend along a relatively straight line. Tip section 75-T is shown oriented, by un-deformed hook segment 74, to extend toward axis 7, such that tip section 75-T and proximal section 75-D enclose an angle φ, which may be about 70 degrees. According to the illustrated embodiment, distal portion hook section 75-H is defined by proximal and distal radii 75-HRp, 75-HRd, and a straight length 75-HS that extends therebetween. In the aforementioned exemplary embodiment of component 700, each hook section proximal radius 75-HRp, when un-deformed, is about 0.040 inch, each hook section distal radius 75-HRd is about 0.030 inch, and each straight length 75-HS is about 0.040 inch; and a length of each tip section 75-T is 0.062 inch±0.005 inch. It is contemplated that this double radius configuration of distal portion hook sections 75-H of component 700 enhances a stability of fixation for device 20 over that of component 300, by a decreased stiffness of tines 703 in proximity to free distal end 752 and additional spring energy to draw each tine 703 further away from the aforementioned second location P2 of penetration through pectinate muscle PM (FIG. 2B).

Figure 6C:
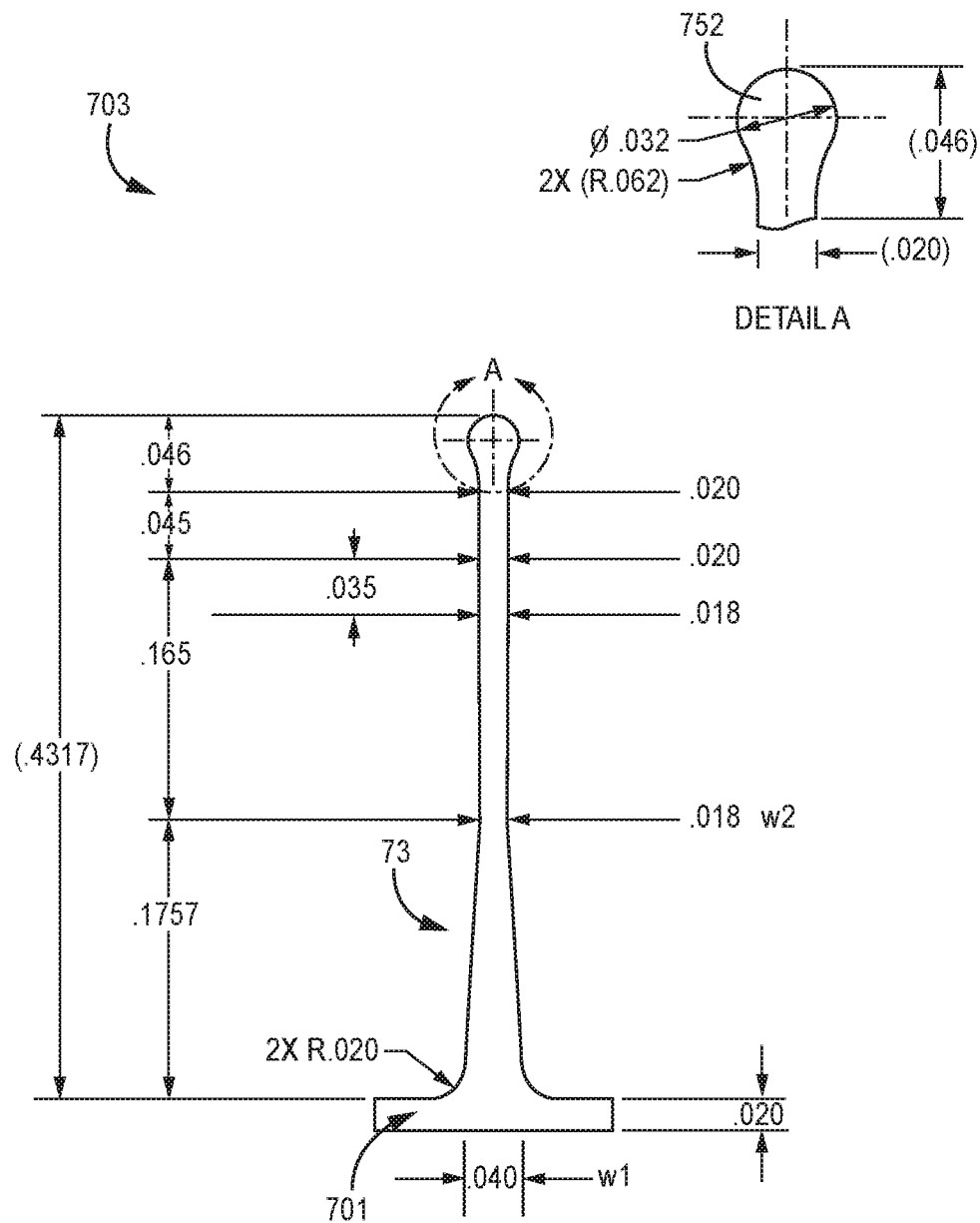
FIG. 6C is a plan view of a portion of the component of FIGS. 6A-B, prior to forming, according to some embodiments.
Figure 6D:
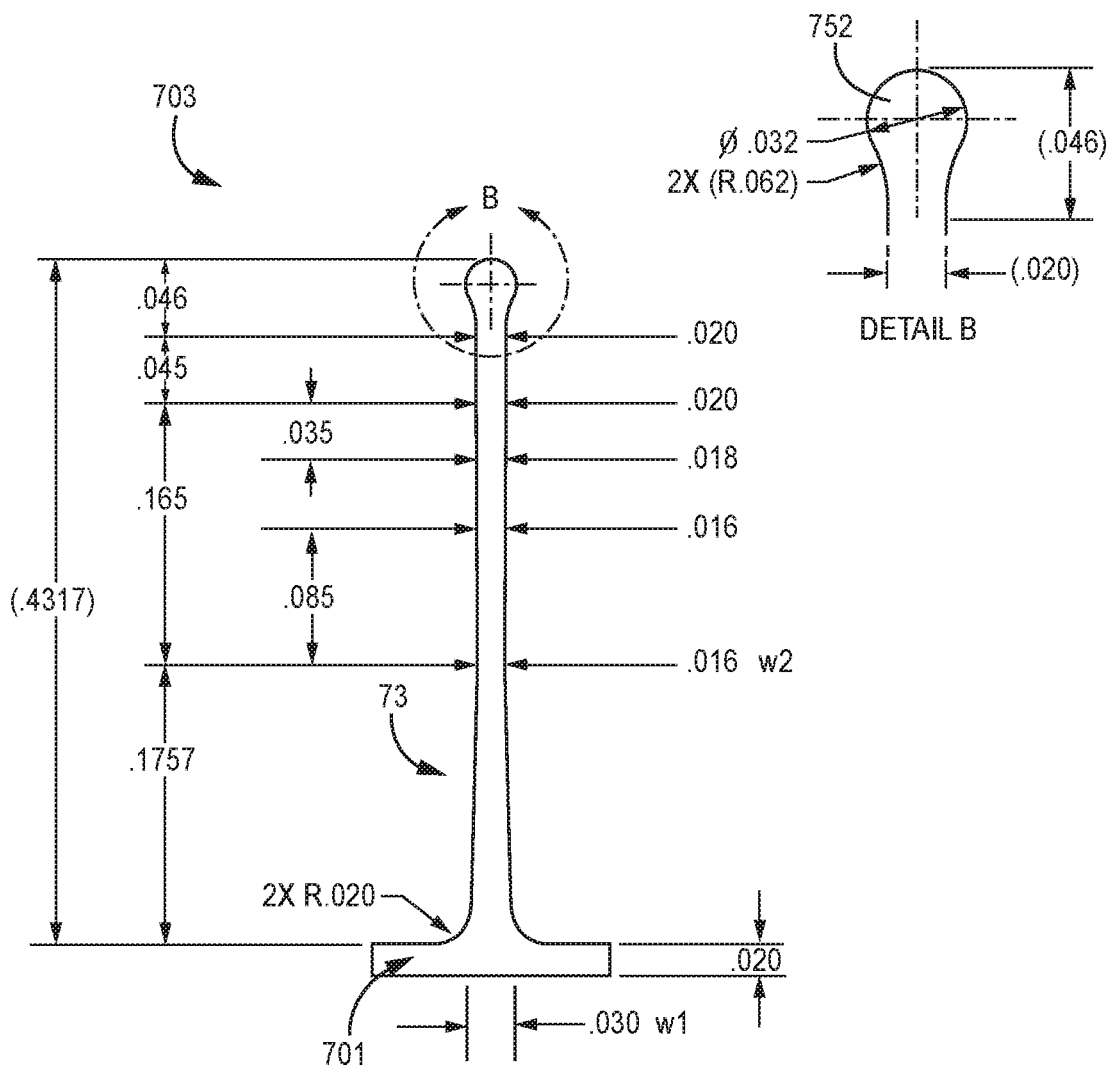
FIG. 6D is a plan view of a portion of the component of FIGS. 6A-B, prior to forming, according to some alternate embodiments.

FIGS. 6C-D are plan views of alternate embodiments of each tine 703, prior to being formed into the configuration of FIG. 6A, wherein exemplary dimensions, in inches, for the alternate embodiments are shown. FIGS. 6C-D illustrate rounded free distal end 752 of each tine 703 having an enlarged width, for example, defined by a diameter of 0.032 inch±0.001 inch. FIG. 6C-D further illustrate a tapering width along a length of each tine 703, wherein proximal, spring portion 73 tapers from a first width w1 in proximity to base to a smaller second width w2. The tapering width may be employed to tailor spring energy and stiffness of tines, for example, to prevent tissue erosion and to enhance the fatigue life of tines 703 over the term of an implant.

In the foregoing detailed description, specific exemplary embodiments have been described. However, it may be appreciated that various modifications and changes can be made without departing from the scope of the invention as set forth in the appended claims.

We claim:

1. A tissue penetrating fixation component for an implantable medical device (IMD), the component comprising:
 a base defining a longitudinal axis of the component and being configured to be fixedly attached to the IMD so that a perimeter of the component extends around an electrode of the IMD, and so that the longitudinal axis of the component is generally aligned along a longitudinal axis of the IMD; and
 a plurality of tines extending from the base and being spaced apart from one another around a perimeter thereof, and each tine of the plurality of tines comprising:
  a proximal portion being fixedly attached to the base, wherein the proximal portion extends from the base in a first direction, and wherein the proximal portion comprises a first pre-formed curvature; and
  a distal portion comprising:
   a proximal section extending from the first pre-formed curvature of the proximal portion in a second direction along a relatively straight line;
   a hook section comprising a second pre-formed curvature extending from the proximal section; and
   tip section extending from hook section toward the longitudinal axis to a free distal end.

2. The component of claim 1, wherein each tine has a constant thickness of about 0.005 inch and a width no less than about 0.02 inch.

3. The component of claim 2, wherein the width of each tine tapers from a greater width in proximity to the base to a lesser width in proximity to the hook section of the distal portion.

4. The component of claim 3, wherein the free distal end of each tine has an enlarged width relative to a remainder of the tip section of the corresponding distal portion.

5. The component of claim 1, wherein the first pre-formed curvature of the proximal portion of each tine is defined by a radius, when undeformed, within a range from about 0.06 inch and about 0.08 inch.

6. The component of claim 1, wherein the tip section of the distal portion of each tine has a length of about 0.06 inch.

7. The component of claim 1, wherein the proximal section of the distal portion of each tine has a length of about 0.1 inch.

8. The component of claim 1, wherein the second preformed curvature of the hook section of the distal portion of each tine is defined by a single radius, when un-deformed, being about 0.05 inch.

9. The component of claim 1, wherein the second preformed curvature of the hook section of the distal portion of each tine, when un-deformed, is defined by two radii and a straight length extending therebetween.

10. The component of claim 1, wherein the proximal section of the distal portion, when undeformed, extends along a relatively straight line that intersects the longitudinal axis at an acute first angle within a range from about 30 degrees and about 50 degrees.

11. The component of claim 10, wherein the acute first angle is about 45 degrees.

12. The component of claim 1, wherein the hook section, when undeformed, orients the tip section to enclose with the proximal section a second angle with in a range from about 70 degrees to about 120 degrees.

* * * * *